United States Patent
Hwang

(10) Patent No.: US 10,495,584 B2
(45) Date of Patent: Dec. 3, 2019

(54) INSPECTION APPARATUS AND INSPECTION METHOD USING THE SAME

(71) Applicant: LG Display Co., Ltd., Seoul (KR)

(72) Inventor: SeokJu Hwang, Incheon (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 15/703,541

(22) Filed: Sep. 13, 2017

(65) Prior Publication Data

US 2018/0188189 A1    Jul. 5, 2018

(30) Foreign Application Priority Data

Dec. 29, 2016    (KR) .......................... 10-2016-082989

(51) Int. Cl.
*G01N 21/17* (2006.01)
*G01N 21/958* (2006.01)
(Continued)

(52) U.S. Cl.
CPC ........... *G01N 21/958* (2013.01); *G01B 11/06* (2013.01); *G01B 11/0625* (2013.01);
(Continued)

(58) Field of Classification Search
CPC .... G01B 11/06; G01N 21/21; G01N 21/8422; G01N 21/958; G01N 2021/1748;
(Continued)

(56) References Cited

U.S. PATENT DOCUMENTS 5,159,412 A * 10/1992 Willenborg ........ G01B 11/0616
250/559.07
5,181,080 A * 1/1993 Fanton ................. G01B 11/065
356/128

(Continued)

FOREIGN PATENT DOCUMENTS

KR    10-2007-0121565 A    12/2007
KR    10-2008-0083414 A     9/2008
(Continued)

OTHER PUBLICATIONS

Decision to Grant dated Sep. 4, 2018 issued in the corresponding Korean Patent Application No. 10-2016-0182989, 5 Pages.
(Continued)

*Primary Examiner* — Isiaka O Akanbi
(74) *Attorney, Agent, or Firm* — Polsinelli PC

(57) ABSTRACT

Disclosed herein is a method for inspecting a transparent film. The method comprises irradiating an inspection target with light using a polarizer, receiving light that is reflected by the inspection target and passes through an analyzer by a line scan camera, synthesizing an amplitude and a phase of wavelength of the light into an intensity of light, comparing the intensity of the light with predetermined intensities of light for inspection targets having different thicknesses; and detecting a defect of the inspection target based on the compared intensity with the predetermined intensities. It can be determined whether there is a transparent film, and the thickness of the transparent film can be measured in a large area. The inspection is carried out in real-time after the (Continued)

transparent film is formed, such that if a defect is generated, it can be fed back immediately to thereby reduce defects.

19 Claims, 8 Drawing Sheets

(51) Int. Cl.
    *G01B 11/06*     (2006.01)
    *G01N 21/84*     (2006.01)
    *G01N 21/21*     (2006.01)
    *G01N 21/95*     (2006.01)
    *G01N 21/88*     (2006.01)

(52) U.S. Cl.
    CPC ......... *G01B 11/0641* (2013.01); *G01N 21/21* (2013.01); *G01N 21/8422* (2013.01); *G01N 21/95* (2013.01); *G01N 2021/1748* (2013.01); *G01N 2021/8427* (2013.01); *G01N 2021/8848* (2013.01); *G01N 2201/0683* (2013.01); *G01N 2201/101* (2013.01)

(58) Field of Classification Search
    CPC ... G01N 2021/8427; G01N 2201/0683; G01N 2201/101
    USPC ................. 356/237.2–237.6, 239.1, 364
    See application file for complete search history.

(56) References Cited

U.S. PATENT DOCUMENTS

| | | | | |
|---|---|---|---|---|
| 5,333,052 A * | 7/1994 | Finarov | .............. | G01B 11/0641 356/369 |
| 6,693,711 B1 * | 2/2004 | Leger | ...................... | G01J 4/00 356/364 |
| 6,934,024 B2 * | 8/2005 | Zhan | ....................... | G01J 4/00 356/369 |
| 6,934,032 B1 * | 8/2005 | Subramanian | ............. | C23F 4/00 156/345.13 |
| 8,411,264 B2 * | 4/2013 | Ueno | ................. | G01N 21/9501 356/237.1 |
| 2002/0107650 A1 * | 8/2002 | Wack | ................... | G01N 21/211 702/81 |
| 2006/0114470 A1 * | 6/2006 | Takashima | ......... | G01B 11/0625 356/453 |
| 2007/0247622 A1 * | 10/2007 | Sun | ........................ | G01N 21/21 356/364 |
| 2007/0296973 A1 | 12/2007 | Kiers et al. | | |
| 2009/0075414 A1 * | 3/2009 | Lee | ...................... | B01J 19/0046 438/49 |
| 2009/0147247 A1 | 6/2009 | Endo et al. | | |
| 2018/0053687 A1 * | 2/2018 | Lee | ................... | H01L 23/53295 |

FOREIGN PATENT DOCUMENTS

| | | |
|---|---|---|
| KR | 10-2009-0038429 A | 4/2009 |
| KR | 10-2014-0012339 A | 2/2014 |
| WO | 2005/010495 A2 | 2/2005 |

OTHER PUBLICATIONS

Office Action dated Feb. 5, 2018 in a Korean Patent Application No. 10-2016-0182989.

Office Action dated Jul. 31, 2019 in connection with the counterpart CN Application No. 201710953566.X (9 pages) and English language translation (9 pages).

\* cited by examiner

INSPECTION APPARATUS AND INSPECTION METHOD USING THE SAME

CROSS-REFERENCE TO RELATED APPLICATION

This application claims the priority of Korean Patent Application No. 10-2016-0182989 filed on Dec. 29, 2016, in the Korean Intellectual Property Office, the disclosure of which is incorporated herein by reference in its entirety.

BACKGROUND

Field of the Disclosure

The present disclosure relates to an inspection apparatus and an inspection method using the apparatus, and more specifically, to an inspection apparatus for determining on existence of a residual layer of a transparent film formed on a substrate for an organic light emitting panel and for measuring the thickness, and an inspection method using the apparatus.

Description of the Background

Display devices provide a variety of information graphically on a screen and are the core technology of the era of information and communications. Such display devices are becoming thinner, lighter and portable, along with higher performance. Among them, an organic light emitting display device is attracting attention, which displays images by controlling the amount of light emitted from an organic light emitting element.

An organic light emitting element can emit layer in its own by using a thin emission layer between electrodes and has an advantage in that it can be made thinner. Generally, an organic light emitting display device has a substrate on which pixel-driving circuits and organic light emitting elements are formed. As the light emitted from the organic light emitting element transmits the substrate or a barrier layer, images are displayed.

An organic light emitting display device includes an organic light emitting element including an organic emission layer, an anode and a cathode, driving elements for driving the organic light emitting element such as a transistor and a capacitor. In detail, an organic light emitting display device utilizes the phenomenon that holes injected from an anode and electrons injected from a cathode recombine in an organic emission layer to form excitons, and light of a particular wavelength is generated as energy is released when the excitons relax from the excited state to the ground state. Accordingly, the organic light emitting display device has advantages in that it has fast response speed, high contrast ratio, good luminous efficiency, high brightness and large viewing angle.

Unfortunately, the organic light emitting element can easily deteriorate by internal factors such as deterioration of the electrodes and the emission layer due to oxygen, deterioration by the reaction between the emission layer and interfaces, etc., as well as external factors such as moisture, oxygen, ultraviolet ray and fabricating conditions of the device. Among these, oxygen and moisture introduced from the outside seriously affect the lifetime of the organic light emitting display device, and thus encapsulation of the device is very important. Accordingly, in order to suppress the oxygen and the moisture from permeating into such an organic light emitting layer, various techniques for sealing an organic light emitting element are currently being used.

SUMMARY

Recently, a flexible organic light emitting display device is being developed by employing a flexible substrate formed of a flexible material such as plastic, such that it can display images even when it is bent. Accordingly, an encapsulation layer also has a flexible structure. Since the flexible organic light emitting display device is advantageous for bending and folding, the bezel of the display device may be reduced by bending a part of the panel. Herein, the bent part of the panel is referred to as a bending area.

In order to seal the organic light emitting element, a process of forming an encapsulation layer on a mother substrate on which a pixel driving circuit and an organic light emitting element are formed for each of a plurality of cells for forming panels is carried out. After the encapsulation layer is deposited on the mother substrate, a process of scribing is carried out to cut the mother substrate into cells.

The encapsulation layer may be formed of a metal film, a glass substrate, a plastic, an organic layer, an inorganic layer, or the like. In detail, the organic layer and the inorganic layer are formed of transparent materials and are deposited on the mother substrate. A mask having openings is used at the position where the encapsulation layer is to be deposited. Although the mask disposed on the substrate for depositing the encapsulation layer is fabricated with a fabrication tolerance, the area of the deposition position may be increased or decreased due to thermal deformation or the like. In detail, the margin of the area where the encapsulation layer is to be deposited is reduced as the bezel of the organic light emitting display devices is reduced. And, the cell type mask is used, which is more easily affected by thermal deformation. In this case, the area of the deposition position of the encapsulation layer may be easily changed.

The organic layer or the inorganic layer may be formed of a material having a viscosity similar to that of water. If so made, the organic layer or the inorganic layer may be formed by inkjet printing. When the viscosity of the material is low, the material is more likely to flow. Accordingly, in order to deposit the organic layer or the inorganic layer at a desired position, it is necessary to appropriately adjust the amount of the material to be applied. If it fails to adjust the amount of the applied material, the material may flow out of the position where the organic layer or the inorganic layer is to be formed.

In this case, the organic layer or the inorganic layer of the encapsulation layer may cross over the above-described bending area or the scribing lines. The portion of the encapsulation layer formed in the bending area or the scribing lines may be damaged if the bending area is bent or the substrate is cut along the scribing lines. In this case, the organic light emitting element may deteriorate due to the damaged encapsulation layer. Unfortunately, it is not checked whether the deposition position of the encapsulation layer is correct until a light inspection process is carried out after the mother substrate is cut. In other words, it is not checked whether there is a defect in real-time, and thus it takes time to feed back the cause of the defect to the equipment for depositing the encapsulation layer, thereby incurring more cost.

And, as the encapsulation layer protects the organic light emitting display device, it is important to keep or maintain the encapsulation layer from being damaged. Accordingly, it is necessary to detect any chance to damage the encapsulation layer in advance during a process of forming the encapsulation layer as well as during subsequent processes after the process.

In view of the above, the inventor of the present disclosure has recognized the above-described problems, and have devised an inspection apparatus for determining whether there is a residual layer and for measuring the thickness of the encapsulation layer after it is deposited in real-time so as to reduce the number of defective panels, and an inspection method using the apparatus.

An aspect of the present disclosure is to provide an inspection apparatus for determining whether an inspection target is deposited across the entire area of the substrate and the thickness of the inspection target.

Another aspect of the present disclosure is to provide an inspection method for determining whether an inspection target is deposited and the thickness of the inspection target in real-time.

It should be noted that objects of the present disclosure are not limited to the above-described aspects, and other objects of the present disclosure will be apparent to those skilled in the art from the following descriptions.

According to an aspect of the present disclosure, there is provided an inspection method comprises irradiating an inspection target with light using a polarizer, receiving reflective light that is reflected by the inspection target and passes through an analyzer by a line scan camera, synthesizing an amplitude and a phase of wavelength of the reflective light into an intensity of light, comparing the intensity of the light with predetermined intensities of light for inspection targets having different thicknesses, and detecting a defect of the inspection target based on the compared intensity with the predetermined intensities. It can be determined whether there is a transparent film, and the thickness of the transparent film can be measured across the entire area of the substrate. The inspection is carried out in real-time after the transparent film is formed, such that if a defect is generated, it can be fed back immediately to the processing equipment, to thereby reduce defects. In this case, the processing cost can be saved.

According to another aspect of the present disclosure, there is provided an inspection apparatus comprises a polarizer linearly polarizing light emitted from a light source, an analyzer allowing the light reflected by an inspection target that passes through the polarizer to transmit, an optical inspection unit including a line scan camera that receives the light transmitted the analyzer and synthesizes an amplitude and a phase of wavelength of the reflected light into an intensity of light, and a detection unit comparing the intensity of the light with predetermined intensities of light for inspection targets having different thicknesses and detecting a defect of the inspection target based on results of the comparing. The recognition of the transparent film can be improved, and the entire area of the substrate can be inspected. In this case, it is possible to effectively determine whether there is a transparent film and to measure the thickness.

The details of one or more aspects of the inspection target matter described in this specification are set forth in the accompanying drawings and the description below.

According to the aspects of the present disclosure, by disposing a polarizer and an analyzer in an inspection apparatus for inspecting a substrate formed of a transparent film, the recognition of the transparent film can be improved, such that it can be effectively determined whether there is the transparent film.

According to the aspects of the present disclosure, by including a scan camera in the inspection apparatus, scan inspection rather than spot inspection can be carried out, such that the portions where the transparent film should not be deposited can be scanned along the periphery of a plurality of cells, thereby reducing defects.

According to the aspects of the present disclosure, the inspection equipment includes a light source emitting light having a wavelength of 400 nm to 800 nm, such that the recognition of the transparent film, which is out of range of visible light, can be improved, thereby effectively determining whether there is the transparent film.

According to the aspects of the present disclosure, the inspection apparatus includes a beam splitter, such that light passing through the polarizer can be incident on an inspection target at right angle, thereby efficiently implementing the inspection apparatus.

According to the aspects of the present disclosure, after an inspection target is formed on the substrate and before the post-process of cells or the module process, it is check whether there is a residual layer of the inspection target and the thickness of the residual layer is measured, such that it is possible to reduce missing a defect during image inspection or reliability inspection, thereby saving the cost.

The Summary is not to specify essential features of the appended claims, and thus the scope of the claims is not limited thereby.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Figure 1:
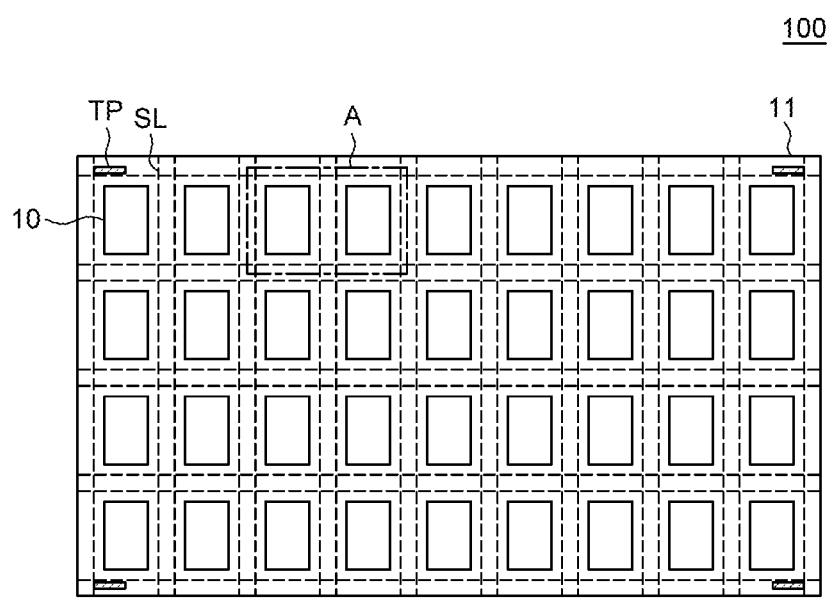
FIG. 1 is a view showing a mother substrate according to an aspect of the present disclosure.

Advantages and features of the present disclosure and methods to achieve them will become apparent from the descriptions of aspects herein below with reference to the accompanying drawings. However, the present disclosure is not limited to aspects disclosed herein but may be implemented in various different ways. The aspects are provided for making the disclosure of the present disclosure thorough and for fully conveying the scope of the present disclosure to those skilled in the art. It is to be noted that the scope of the present disclosure is defined only by the claims.

The figures, dimensions, ratios, angles, the numbers of elements given in the drawings are merely illustrative and are not limiting. Like reference numerals denote like elements throughout the descriptions. And, in describing the present disclosure, descriptions on well-known technologies may be omitted in order not to unnecessarily obscure the gist of the present disclosure. It is to be noticed that the terms "comprising," "having," "including" and so on, used in the description and claims, should not be interpreted as being restricted to the means listed thereafter unless specifically stated otherwise. Where an indefinite or definite article is used when referring to a singular noun, e.g. "a," "an," "the," this includes a plural of that noun unless specifically stated otherwise.

In describing elements, they are interpreted as including error margins even without explicit statements.

In describing positional relationship, such as "an element A on an element B," "an element A above an element B," "an element A below an element B" and "an element A next to an element B," another element C may be disposed between the elements A and B unless the term "directly" or "immediately" is explicitly used.

In describing temporal relationship, terms such as "after," "subsequent to," "next to" and "before" are not limited to "directly after," "directly subsequent to," "immediately next to" "immediately before," and so on, unless otherwise specified.

The terms first, second, third and the like in the descriptions and in the claims are used for distinguishing between similar elements and not necessarily for describing a sequential or chronological order. These terms are used to merely distinguish one element from another. Accordingly, as used herein, a first element may be a second element within the technical idea of the present disclosure.

Features of various aspects of the present disclosure may be combined partially or totally. As will be clearly appreciated by those skilled in the art, technically various interactions and operations are possible. Various aspects can be practiced individually or in combination.

Hereinafter, an inspection apparatus and an inspection method according to aspects of the present disclosure will be described in detail with reference to the accompanying drawings. In the following description, a mother substrate including a plurality of cells to form organic light emitting panels will be described as an aspect of an inspection target by the inspection apparatus.

FIG. 1 is a view showing a mother substrate 100 according to an aspect of the present disclosure.

The mother substrate 100 includes a plurality of cells 10 each corresponding to the respective organic light emitting panels. That is, the cells 10 are cut into organic light emitting panels. Although the cells 10 are shown as having a rectangular shape in FIG. 1, this is merely illustrative. The cells 10 may have a variety of shapes such as a circular shape. Scribing lines SL for separating the cells 10 from one another are formed around each of the cells 10. The scribing lines SL may be actually drawn on the substrate 11 or virtual scribing lines SL may be defined by connecting alignment keys or any marks around the cells 10.

In the display area formed in each of the cells 10, a pixel driving circuit is disposed. The pixel driving circuit may include a transistor, a capacitor, etc.

Test patterns TP may be disposed around the substrate 11. Test patterns TP may be located on the outer side of the scribing lines SL. Each of the test patterns TP serves to indicate the positions so that films of the encapsulation layer for encapsulating the cells 10 can be separately deposited to adjust the thickness of the films. For example, if the encapsulation layer includes a first encapsulation layer, a second encapsulation layer, and a third encapsulation layer, the test patterns TP may include a first test pattern for forming the first encapsulation layer, a second test pattern for forming the second encapsulation layer, and a third test pattern for forming the third encapsulation layer disposed on the substrate 11 by repeating processes of forming them. The first encapsulation layer may be formed by using a mask having openings positioned at the locations where the plurality of cells 10 and the first test pattern are to be formed. The second encapsulation layer may be formed by using a mask having openings positioned at the locations where the plurality of cells 10 and the second test pattern are to be formed. The third encapsulation layer may be formed by using a mask having openings positioned at the locations where the plurality of cells 10 and the third test pattern are to be formed. Two or more layers may be formed in the test patterns TP depending on the properties of the encapsulation layer. Accordingly, the thickness of the first encapsulation layer may be measured with the first test pattern, the thickness of the second encapsulation layer may be measured with the second test pattern, and the thickness of the third encapsulation layer may be measured with the third test pattern. And, the uniformity of the encapsulation layer can be checked with the test patterns TP formed along the periphery of the substrate 110.

A cell-type mask having openings each for the respective cells 10, or a line-type mask having openings each for the respective rows or columns of the cells 10 may be used.

Although FIG. 1 shows the test patterns TP formed only at the four corners of the substrate 11, it is merely illustrative. As mentioned above, the first test pattern, the second test pattern and the third test pattern are repeatedly disposed on the upper and lower surfaces of the substrate 11 or along the periphery of the substrate 11, and the thicknesses of the first encapsulation layer, the second encapsulation layer and the third encapsulation layer may be measured, thereby ensuring the uniformity of the thickness of each encapsulation layer.

Hereinafter, the cells 10, and the positions of an encapsulation layer in each of the cells 10 and scribing lines SL will be described in detail.

Figure 2:
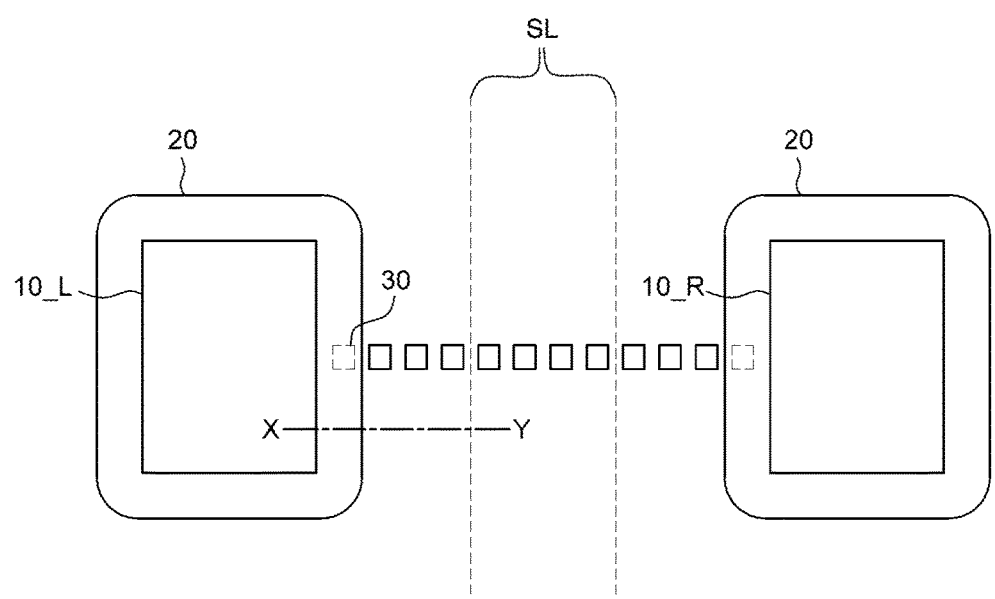
FIG. 2 is an enlarged view of portion A of FIG. 1.

FIG. 2 is an enlarged view of portion A of FIG. 1. Portion A includes two cells 10_L and 10_R.

In each of the two cells 10_L and 10_R, a pixel driving circuit and an organic light emitting element are formed on the substrate 11. In order to protect the pixel driving circuit and the organic light emitting element, the encapsulation layer 20 is formed so as to cover each of the two cells 10_L and 10_R. The scribing lines SL are defined between the left cell 10_L and the right cell 10_R. After forming the encapsulation layer 20 on the substrate 11, the substrate 11 may be cut along the scribing lines SL.

A plurality of metal keys 30 may be disposed between the left cell 10_L and the right cell 10_R in order to cut the substrate 11 or to check if the encapsulation layer 20 has crossed over the scribing lines SL. Twelve metal keys 30 are formed in FIG. 2, for example. Although FIG. 2 shows the left first metal key and the right first metal key are covered by the encapsulation layers 20, it may not be an essential feature of the present disclosure. Although FIG. 2 shows that the scribing line SL for the left cell 10_L is located between the fourth metal key and the fifth metal key from the left, and the scribing line SL for the right cell 10_R is located between the fourth metal key and the fifth metal key from the right, the positions of the scribing lines SL are not limited thereto.

The substrate 11 may be cut with laser along the scribing lines SL set with respect to the metal keys 30. If the encapsulation layer 20 is deposited crossing over the scribing line SL, the encapsulation layer 20 may be cut by the laser, such that the encapsulation layer 20 may be peeled off. Even if the substrate 11 is cut by any other method than the laser, once the encapsulation layer 20 is cut such that its cross-section is exposed, the encapsulation layer 20 may be peeled off. In this case, moisture or oxygen may permeate through the cross section of the encapsulation layer 20, thereby resulting in damage or deterioration of the organic light emitting element. Therefore, it is necessary to inspect whether the encapsulation layer 20 has crossed over the scribing lines SL.

In order to check if the encapsulation layer 20 of the left cell 10_L crossed over the scribing line SL, it may be detect whether the encapsulation layer 20 is formed on the metal keys 30 located on the inner side (left side) of the scribing line SL. For example, it may be determined that the encapsulation layer 20 is defective if a residual layer of the encapsulation layer 20 is detected on the left third metal key. Like the left cell 10_L, in the right cell 10_R, it may be determined that the encapsulation layer 20 is defective if a residual layer of the encapsulation layer 20 is detected on the right third metal key.

A method for detecting a residual layer of the encapsulation layer 20 is as follows: The intensities of the metal keys 30 and the intensities of the regions other than the metal keys 30 are detected, to determine the metal keys 30 covered by the encapsulation layer 20 or the edge of the encapsulation layer 20. To this end, an optical inspection unit is used. The optical inspection unit can detect the intensities of the metal keys 30 through optical analysis by observing the metal keys 30 and display them as an image. For example, let us assume that the left third metal key is covered by the encapsulation layer 20, and the fourth left metal key is not covered by the encapsulation layer 20. The optical inspection unit inspects whether the encapsulation layer 20 is formed on the metal keys 30 and informs that the third metal key is covered by the encapsulation layer 20. And, the optical inspection unit may display the first, second and third metal keys from the left side as darker images than the subsequent metal keys. Then, it is inspected whether the encapsulation layer 20 is formed in any other region than the metal keys 30, to inform that the edge of the encapsulation layer 20 is formed between the third metal key and the fourth metal key, or to indicate the distance from the cell 10_L to the encapsulation layer 20. And, the optical inspection unit may display the edge line of the encapsulation layer 20 between the left third metal key and the left fourth metal key as a dark image.

The metal keys 30 not only indicate the inspection positions but also obtaining recognition when displaying the analysis result as an image. However, the optical inspection unit can detect whether there is the encapsulation layer 20 even without the metal keys 30. Without the metal keys, however, the inspection position is not indicated, and thus it take more time to detect, and it may be difficult for the inspector to recognize the inspection result through the image.

The optical inspection unit and the principle of analysis for detecting the intensity will be described later.

As described above, the metal keys 30 may be formed in one line at the center between the left cell 10_L and the right cell 10_R, but this is not limiting. And, the metal keys 30 may be formed in multiple lines. For example, the metal keys 30 may be formed in two lines, one at the upper portion and the other at the lower portion of the cells 10. And, the metal keys 30 may be formed in three lines, one at the upper portion, another at the middle portion and the other at the lower portion of the cells 10.

Therefore, the encapsulation layer 20 should be deposited so as not to cross over the scribing lines SL, and it should be possible to check if the encapsulation layer 20 crosses over the scribing lines SL after it has been formed. By detecting a defect of the encapsulation layer 20 in real-time after the encapsulation layer 20 has been formed, and immediately feeding back the result to the processing equipment used for forming the encapsulation layer 20, the yield can be improved and thus it is possible to reduce the rejection rate and to save processing cost.

Although the method of checking the scribing lines SL with respect to the metal keys 30 has been described above, the scribing lines SL may be checked with additional marks other than the metal keys 30.

Figure 3:
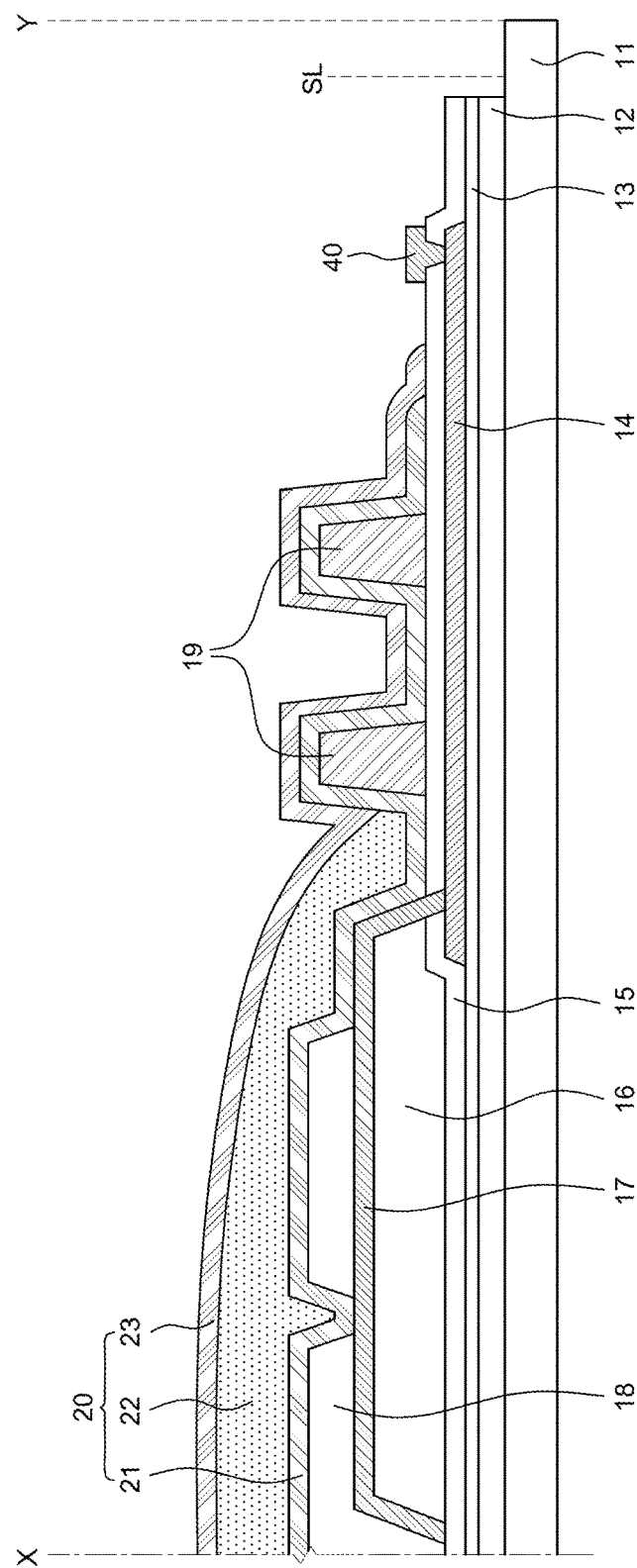
FIG. 3 is a cross-sectional view taken along line X-Y of FIG. 2.

FIG. 3 is a cross-sectional view taken along line X-Y of FIG. 2. Description will be made with reference to FIG. 3 in conjunction with FIG. 2.

A buffer layer 12 may be disposed on the substrate 11, and a first insulating layer 13 may be formed on the buffer layer 12. The substrate 11 may be formed of an insulating material, and may be a flexible substrate formed of, for example, glass, polyimide, acryl, polyacrylate, polycarbonate, polyether, sulfonic acid-based material, or a silicon oxide ($SiO_x$) material having flexibility.

And, the organic light emitting display device according to aspects of the present disclosure may be applied to a variety of display devices including a TV, a mobile device, a tablet PC, a monitor, a laptop computer, an automotive display device, etc. And, the organic light emitting display device may also be applied to a wearable display device, a foldable display device, a rollable display device, a bendable display device, etc. And, if the substrate 11 is a flexible substrate, the organic light emitting display device may be applied to a curved display device, a foldable display device, a rollable display device, a bendable display device, an automotive display device, etc.

The buffer layer 12 enhances the adhesion between the layers formed thereon and the substrate 11 and may block moisture or oxygen permeating through the substrate 11. The buffer layer 12 may include a first buffer layer or a second buffer layer. The first buffer layer may be a multi-buffer. The second buffer layer can protect an active layer of a thin-film transistor and suppress various kinds of defects. The multi-buffer may be formed by alternately stacking silicon oxide ($SiO_2$) and silicon nitride ($SiN_x$), and may suppress the diffusion of moisture and/or oxygen permeating into the substrate 101. The second buffer layer may be an active-buffer. The second buffer layer may be formed of amorphous silicon (a-Si) or the like. The buffer layer 12 may include both of the first buffer layer and the second buffer layer or may include one of the first buffer layer and the second buffer layer. It is to be noted that the buffer layer 12 is not an essential element and may be eliminated depending on the type and material of the substrate 11, the structure and type of the thin-film transistor, etc. The buffer layer 12 may be formed of multiple layers.

The first insulating layer 13 may be disposed on the buffer layer 12. Since the first insulating layer 13 may be formed on a gate electrode disposed on the buffer layer 12, it may also be referred to as a gate insulating film.

A source/drain electrode 14 may be disposed on the first insulating layer 13. The source/drain electrode 14 may be used as a connection electrode for transmitting a voltage applied from an external source through a pad 40 to the pixel driving circuit disposed in the cell 10. The pad 40 may be formed of, but is not limited to, the same material as an anode 17 via the same process. The anode 17 may be in contact with the source/drain electrode 14 through a contact hole formed in a second insulating layer 15. A driver IC, a flexible printed circuit board (FPCB), a chip on plastic (COP), or a chip on film (COF) may be attached to the pad 40.

The second insulating layer 15 is disposed on the source/drain electrode 14. On the second insulating layer 15, a planarization layer 16 may be disposed, which eliminates step height differences generated by the thin-film transistor, etc., formed in the cell 10. The anode electrode 17 may be disposed on the planarization layer 16. The anode electrode 17 may be in contact with the source/drain electrode 14 through the contact hole formed in the second insulating layer 15. The anode electrode 17 may also be used as a connection electrode for transmitting a voltage applied from an external source through the pad 40 to the inside of the cell 10. For example, the voltage may be, but is not limited to, a high-potential voltage (VDD), a low-potential voltage (VSS), or a data voltage (Vdata).

The buffer layer 12, the first insulating layer 13 and the second insulating layer 15 may be formed of a single layer of silicon nitride ($SiN_x$), silicon oxide ($SiO_x$) or silicon oxynitride ($SiO_xN_x$), or multiple layers of silicon nitride ($SiN_x$), silicon oxide ($SiO_x$) and silicon oxynitride ($SiO_xN_x$). The source/drain electrode 14 may be formed of one of various metal materials including molybdenum (Mo), aluminum (Al), chromium (Cr), gold (Au), titanium (Ti), nickel (Ni), neodymium (Nd) and copper (Cu), an alloy of two or more thereof, or multiple layers thereof. The first planarization layer 16 may be formed of, but is not limited to, one of acrylic resin, epoxy resin, phenol resin, polyamide resin, polyimide resin, unsaturated polyester resin, polyphenylene resin, polyphenylene sulfide resin, benzocyclobutene and photoresist.

A bank 18 for separating an emission region from one another may be formed on the anode electrode 17 formed in the cell 10. An organic emission layer is disposed on the bank 18 and on the portion of the anode not covered by the bank 18. A cathode is disposed on the organic emission layer and the bank 18.

A spacer may be disposed on the bank 18. The spacer can prevent damage to the organic light emitting element that may occur by a fine metal mask (FMM) used during the process of patterning the organic emission layer.

The bank 18 is disposed on a part of the anode electrode 17 formed outside the cell 10. The encapsulation layer 20 is disposed on the bank 18 so as to seal the cell 10 and may include a first encapsulation layer 21, a second encapsulation layer 22, and a third encapsulation layer 23. In order to seal the pixel driving circuit and the organic light emitting element effectively, the first encapsulation layer 21 and the third encapsulation layer 23 may be formed of an inorganic material while the second encapsulation layer 22 may be formed of an organic material such as a polymer. The first encapsulation layer 21 and the third encapsulation layer 23 may be silicon oxide ($SiO_x$), silicon nitride ($SiN_x$), or silicon oxynitride ($SiO_xN_x$).

The second encapsulation layer 22 is also referred to as a particle cover layer (PCL) and may cover particles. For example, if the third encapsulation layer 23 formed of an inorganic material is disposed on the surface of the first encapsulation layer 21 where particles are attached, without the second encapsulation layer 22 formed of an organic material, there may be a gap around the particles since the inorganic material does not have strong adhesive force with the particles on the surface of the first encapsulation layer 21. Accordingly, the encapsulation layer 20 may be peeled off due to this gap. For this reason, the second encapsulation layer 22 formed of an organic material is disposed between the first encapsulation layer 21 and the third encapsulation layer 23, such that it is possible to prevent the encapsulation layer 20 from being peeled off by covering the particles and the periphery of the particles.

The first encapsulation layer 21 and the third encapsulation layer 23 formed of an inorganic material may be formed by deposition. For example, they may be formed by a chemical vapor deposition (CVD) method or an atomic layer deposition (ALD) method. In the chemical vapor deposition method, a material to be deposited is introduced into a chamber and then deposited at a desired region, which is not covered by a mask. The material of the encapsulation layer 20 is applied to the cell 10 and the nearby regions to seal the cell 10. However, the pad 40 to which external signals are applied and the scribing lines SL on the substrate 11 have to be covered with a mask so that the material is not be applied over them. As mentioned above, if there is a residual layer of the encapsulation layer 20 on the scribing line SL, the cross-section of the encapsulation layer 20 is exposed when the encapsulation layer 20 is cut by laser, such that the encapsulation layer 20 may be peeled off. And, if there is a residual layer of the encapsulation layer 20 on the pad 40, the drive IC, the flexible printed circuit board, the COP or COF may be poorly attached, and electrical signals may be erroneously input. And, when the organic light emitting panels formed by separating the cells 10 from one another are used as a foldable display device, a bendable display device or a rollable display device having a bending area, i.e., a part of the panel that is bent or folded, if there is a residual layer of the encapsulation layer 20 in the bending area, a crack may be generated in the encapsulation layer 20 during the process of bending or folding a part of the panel. In this case, moisture or oxygen may permeate through the crack to deteriorate the organic light emitting element. Therefore, the residual layer of the encapsulation layer 20 should not be formed on the scribing lines SL, the pad 40, and the bending area.

And, when a plurality of touch electrodes is formed on the encapsulation layer 20 in order to configure a touch functionality, there may arise a problem that a short-circuit can be formed between the touch electrodes if the encapsulation layer 20 is cracked or defective. Accordingly, it is necessary to make sure that no residual layer or spot is generated on the encapsulation layer 20.

The mask used for forming the first encapsulation layer 21 and the third encapsulation layer 23 is fabricated such that it has openings positioned at locations other than those where the scribing lines SL, the pad 40 and the bending area are to be located. However, the openings may be enlarged or reduced if they are deformed by the heat applied during the processes, such that the first encapsulation layer 21 and the third encapsulation layer 23 may cross over the scribing lines SL, the pad 40 and the bending area. Accordingly, it is necessary to check if the first encapsulation layer 21 and the third encapsulation layer 23 have crossed over the scribing lines SL, the pad 40 and the bending area after the third encapsulation layer 23 is formed.

Since the second encapsulation layer 22 is an organic material, it may be applied using inkjet printing. Inkjet printing can be carried out faster with less material loss than screen printing. And, inkjet printing allows for thin film, and thus is advantageous for a foldable display device, a bendable display device or a rollable display device. And, by inkjet printing, it is easy to control the location where the second encapsulation layer 22 is to be formed, to thereby reduce the bezel area. However, since ink is used as application material, the viscosity is similar to that of water and accordingly it may flow. Thus, a dam 19 may be disposed around the cell 10 to limit the forming region in the second encapsulation layer 22. The dam 19 can suppress overflow of the second encapsulation layer 22 and may have a single structure or a double structure depending on the height by which the second encapsulation layer 22 is applied and the height of the dam 19. More than one dam 19 may be formed.

The height of the second encapsulation layer 22 may be increased to prevent the foreign matter from being peeled off by particles. However, as the height of the second encapsulation layer 22 increases, the number of the dam 19 or the height of the dam 19 also has to be increased. And, if it fails to adjust the amount of the organic material to apply to form the second encapsulation layer 22, the organic material may flow over the dam 19 to invade the scribing line SL, the pad 40 or the bending area. Accordingly, it may need to detect the overflow of the second encapsulation layer 22 as well.

Figure 4:
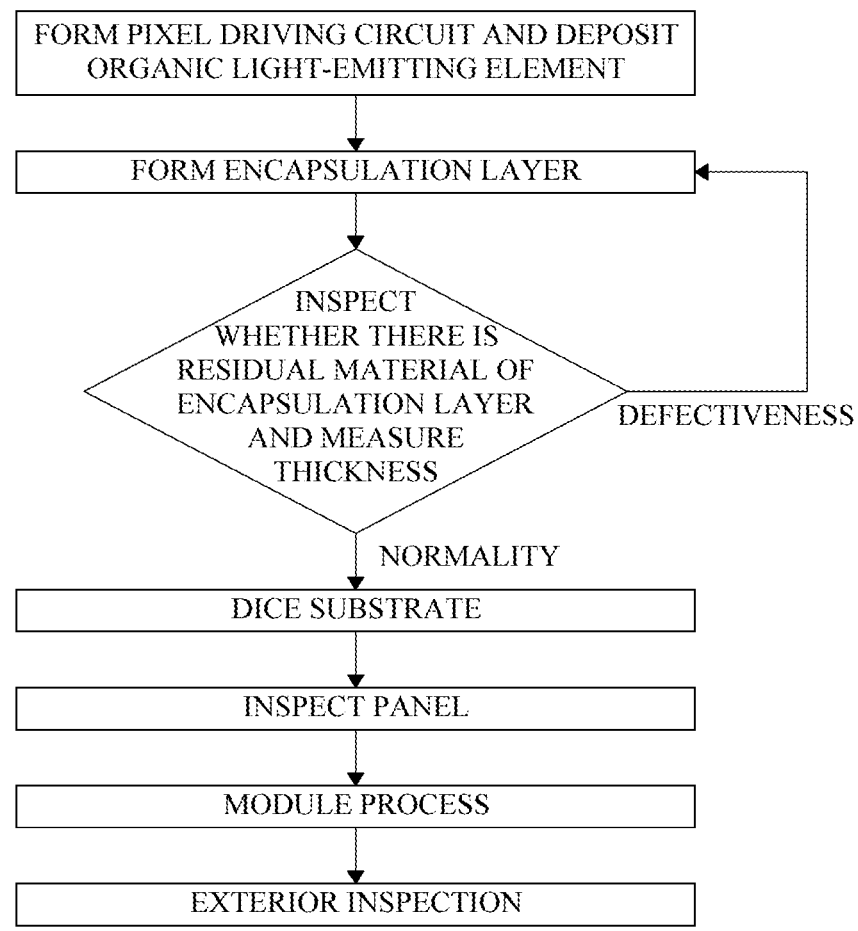
FIG. 4 is a flowchart for illustrating processes of fabricating and inspecting an organic light emitting panel according to an aspect of the present disclosure.

FIG. 4 is a flowchart for illustrating processes of fabricating and inspecting an organic light emitting panel according to an aspect of the present disclosure. The fabricating process of organic light emitting panels will be described with reference to FIGS. 1 to 3, and inspections necessary for each of the fabricating processes will be described. A pixel driving circuit is formed in each of the cells 10 separately formed on the substrate 11. On the pixel driving circuit, an organic light emitting element including an anode, an organic emission layer, and a cathode. The organic emission layer may emit red, green or blue light, and may be formed using an organic light emitting material that is a phosphorescent material or fluorescent material. And, the emission layer may include quantum dots (QDs).

Then, an encapsulation layer 20 is formed over the organic light emitting element to seal the cell 10. At this time, the encapsulation layer 20 may be formed of a single layer or multiple layers of two or more layers.

After the encapsulation layer 20 has been formed, it is inspected whether the encapsulation layer 20 is applied to the scribing lines SL, the pad 40 and the bending area, and at the same time, the thickness of the encapsulation layer 20 is inspected to achieve the uniformity of the encapsulation layer 20. By carrying out the inspections immediately after forming the encapsulation layer 20, it is possible to improve the yield by immediately giving feedback to the processing equipment used for forming the encapsulation layer 20 when a defect is detected. Accordingly, it is possible to prevent missing a defect during subsequent lighting test or reliability test. In this case, the cost can be saved.

After inspecting a residual layer and the thickness of the encapsulation layer 20, a barrier film may be additionally attached to enhance the lifetime of the organic light emitting panel. It is to be noted that the barrier film may be omitted. Then, the step of cutting the substrate 11 is performed. The substrate 11 is cut along the scribing lines SL into a plurality of organic light emitting panels. Each of the organic light emitting panels separated from the substrate 11 may be a minimum unit capable of working as a display device. Electric signal is applied to the organic light emitting panels to perform a step of detecting defective images such as spot or point defects, line defects, mura, etc. If the step of inspecting a residual layer and the thickness of the encapsulation layer 20 is not carried out after the formation of the encapsulation layer 20, a defect is then detected in the step of inspecting the organic light emitting panels. As used herein, the step of forming the encapsulation layer 20 may be referred to as a pre-process of cells, while the steps of cutting the substrate after forming the encapsulation layer 20 and inspecting the panels may be referred to as post-processes of cells.

After the panels have been inspected, a module process is carried out. The module process is carried out to improve image quality by attaching an optical film, a printed circuit board and a driver IC to the organic light emitting panels, and to apply an external signal to the organic light emitting panels to drive their elements.

After the module process has been completed, the organic light emitting panels are subjected to visual inspection. The visual inspection is carried out to determine whether the components are properly attached during the module process. During visual inspection, it is possible to detect a defect related to reliability of the organic light emitting panels possibly occurring after overall image inspection and aging have been carried out on the panels. If the encapsulation layer 20 has crossed over the scribing lines SL, the pad 40 or the bending area, the encapsulation layer 20 may be cracked, such that a defect in images or reliability defect may occur, which is detected during the visual inspection step.

Accordingly, by inspecting a residual layer and the thickness of the encapsulation layer 20 before the post-processes of cells or before the module process, a feedback signal can be sent in real-time to the processing equipment that forms the encapsulation layer 20. Accordingly, it is possible to prevent missing a defect during the panel inspection or the visual inspection, saving the cost.

Subsequently, an inspection apparatus capable of inspecting a residual layer and the thickness of the encapsulation layer 20 will be described.

Figure 5:
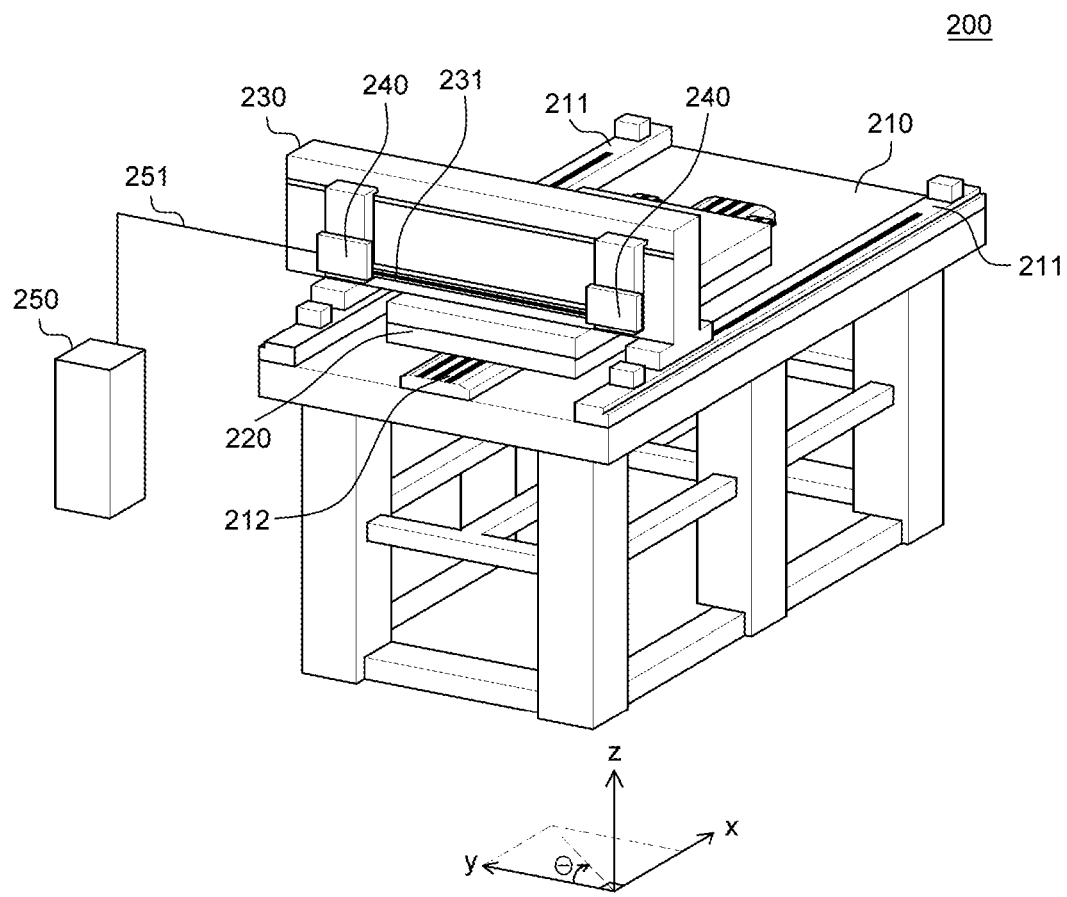
FIG. 5 is a view showing an inspection module to inspect an inspection target according to an aspect of the present disclosure.

FIG. 5 depicts an inspection module 200 to inspect an inspection target according to an aspect of the present disclosure. The module can determine whether there is a residual layer and measure the thickness of the encapsulation layer 20 while it moves along the scribing lines SL, the pad 40 and the bending area. The mother substrate 100 shown in FIG. 1 will be described as an example of the inspection target.

The inspection module 200 may include a stage 210, an x-axis moving rail 211 for moving an optical inspection unit 240 in the x-axis direction, a holder 220 for holding an inspection target, and a holder moving rail 212 for moving the holder 220 in the x-axis direction.

A horizontal structure 230 for mounting the optical inspection unit 240 is disposed on the moving rail 211. The horizontal structure 230 may include a y-axis moving rail 231 by which the optical inspection unit 240 is movable in the y-axis direction. For example, two optical inspection units 240 may be mounted on the horizontal structure 230, such that each of them may inspect the respective scan areas of the inspection target, thereby saving the inspection time. The horizontal structure 230 may also be referred to as a gantry.

In order to suppress the influence by the external environment on the optical inspection unit 240 during the inspection, a chamber of nitrogen atmosphere, which is a glove box, may be installed around the inspection module 200.

The optical inspection unit 240 may move an inspection target along the x-axis and y-axis as desired to inspect whether there is a residual layer and to measure the thickness. The data measured by using the optical inspection unit 240 is transmitted to a detection unit 250 via an optical cable 251 connected to the optical inspection unit 240. The detection unit 250 may include an image processor that analyzes transmitted data and a determiner that determines whether the inspection target is defective based on the analyzed results. And, the inspection module may further include a display device that displays the determination. The display device may be, for example, a computer.

And, the inspection module 200 may include an alignment camera mounted on the horizontal structure 230 so that it senses an alignment mark on an inspection target or the substrate when the inspection target is placed on the holder 220 and aligns the optical inspection unit 240 with the inspection target while moving the holder 220 in the y-axis direction and a theta (θ) direction. And, a driving unit for moving the holder 220 in the y-axis direction and the theta direction is disposed below the holder 220. The driving unit may be, but is not limited to, a linear motor. The inspection module 200 may include an auto focusing unit mounted on the horizontal structure 230 so that it can adjust the focus in real-time, which can be changed while the optical inspection unit 240 moves along the inspection target, by adjusting the distance to the inspection target. The horizontal structure 230 can move along the x-axis, y-axis and z-axis directions along the inspection target. A driving unit for moving the horizontal structure 230 along the x-axis, y-axis and z-axis directions is disposed below the horizontal structure 230. The driving unit may be, but is not limited to, a linear motor.

As mentioned above, the encapsulation layer 20 may be formed of a silicon-based material or a polymer material and may be a transparent film. The transparent film is not easily seen by human naked eyes, and it is difficult to check the existence of the transparent film even with general inspection apparatus. Therefore, the optical inspection unit 240 is used that can detect a defect in the transparent film better.

Figure 6:
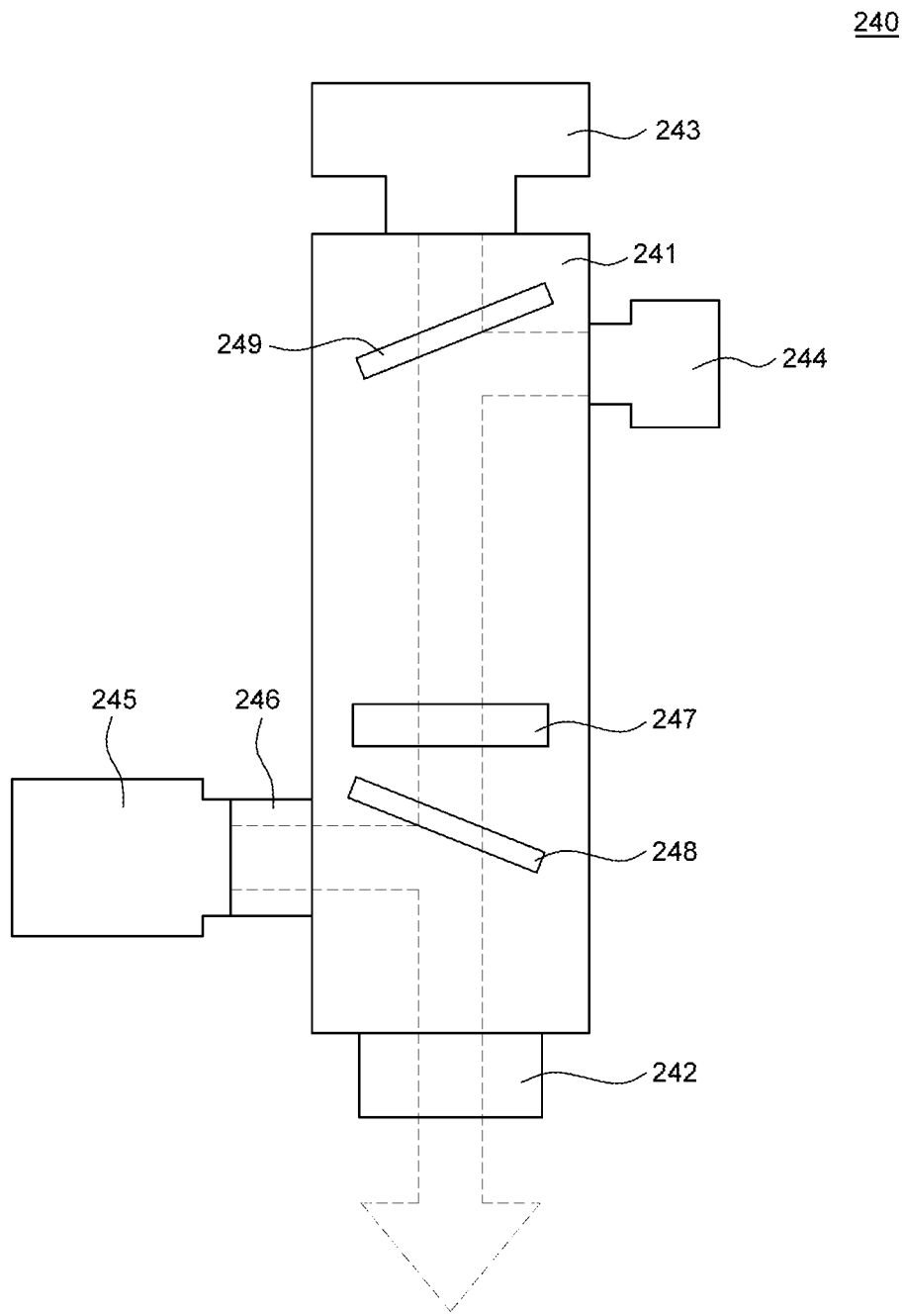
FIG. 6 is a view of the optical inspect unit included in the inspection module shown in FIG. 5.
Figure 7:
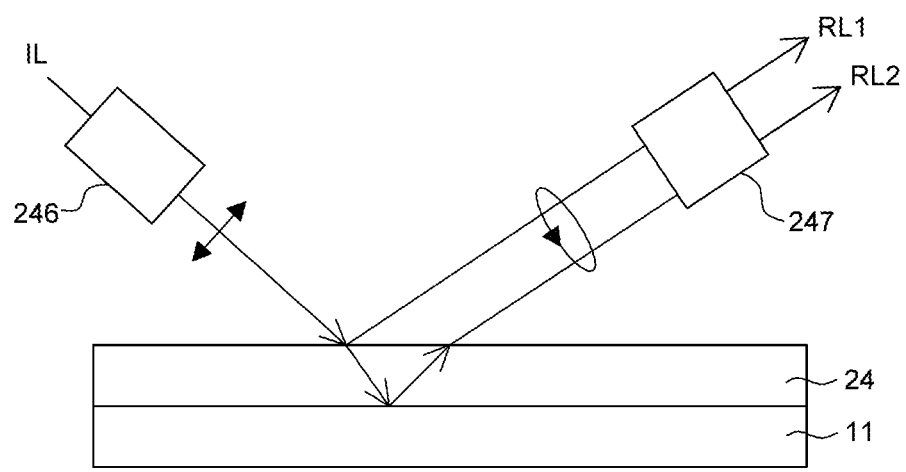
FIG. 7 is a view showing the inspection principle by the inspection apparatus.
Figure 8A:
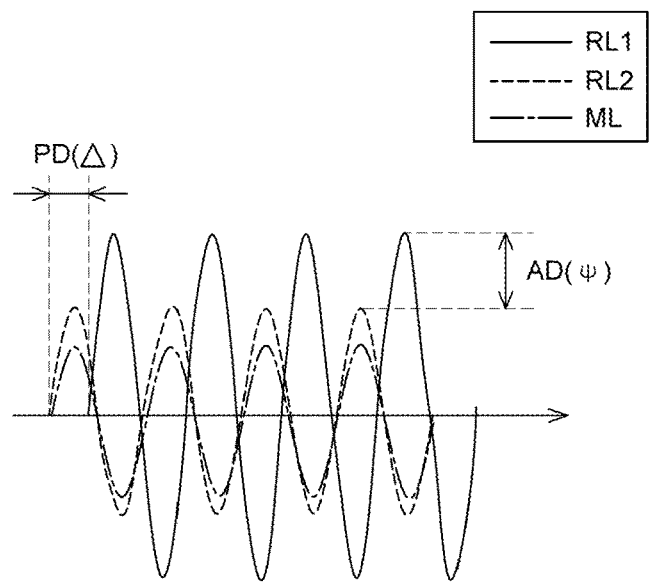
FIG. 8A is a graph showing wavelengths of light passed through a thicker inspection target.
Figure 8B:
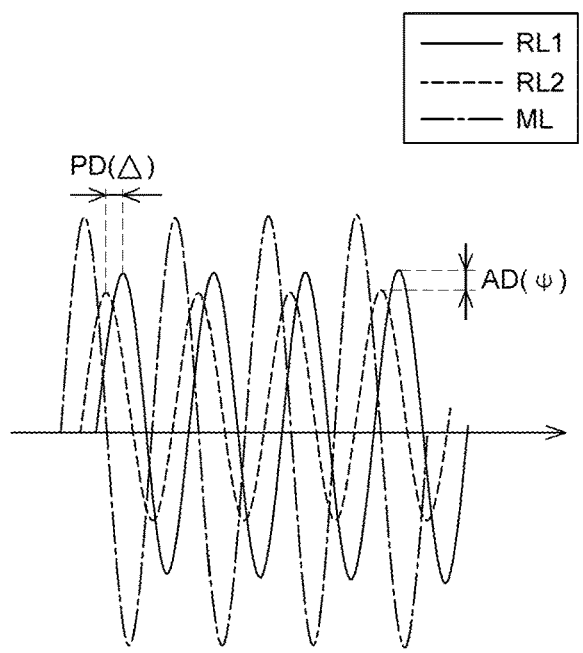
FIG. 8B is a graph showing wavelengths of light passed through a thinner inspection target.

FIG. 6 is a view of the optical inspect unit 240 included in the inspection module 200 shown in FIG. 5. Descriptions will be made with reference to FIG. 7 for illustrating the principle of the optical inspect unit 240 in conjunction with FIGS. 8A and 8B showing the wavelength graphs. According to an aspect of the present disclosure, the optical inspection unit 240 is configured to irradiate light so that it is incident on an inspection target at right angle.

The optical inspection unit 240 may include a line scan camera 243, an auxiliary camera 244, a lens barrel 241 capable of accommodating a plurality of lenses to adjust the optical path, a light source 245, and an observation lens 242.

The line scan camera 243 is capable of observing the area of 8 mm by 8 mm at a time while moving. Therefore, the line scan camera 243 can inspect whether there is the inspection target and measure the thickness of the inspection target for every cell along the periphery. Accordingly, it can be efficient in detecting a defect caused by the residual layer. Since it may take long time to inspect every cell on the mother substrate, the line scan camera 243 may inspect the cells while it moves along the metal keys 30 so as to reduce the time. Alternatively, referring back to FIG. 5, the inspection may be carried out for every cell in the y-axis direction that is the shorter side, while the inspection may be carried out only for the metal keys 30 in the x-axis direction that is the longer side. The substrate may be inspected in many different ways taking into account the processing time.

Since the line scan camera 243 is capable of displaying color images, it may be easy to check if there is the substrate and to measure the thickness.

The auxiliary camera 244 receives light containing the same information as the light received by the line scan camera 243 and assists the line scan camera 243. The initial setting time for the line scan camera 243 may take long for inspecting an inspection target when the inspection target is loaded. Therefore, the auxiliary camera may be used to focus the inspection target on behalf of the line scan camera 243, to thereby save the setting time. As mentioned above, since the auxiliary camera 244 receives the same light as the line scan camera 243, it can be used instead of the line scan camera 243 when the line scan camera fails.

The lens barrel 241 may include at least one lens or a filter. The filter may be a bandpass filter for splitting light from the light source 245 by wavelengths. The light from the light source 245 can be divided into lights in different wavelengths by the bandpass filter. For example, the bandpass filter may output lights of different wavelengths corresponding to red, green, blue and infrared rays, respectively. And, the at least one lens included in the lens barrel 241 may be a magnification lens and a condenser lens or a collecting lens for condensing the light, etc. For example, a magnification lens may include a high magnification lens.

The wavelength of the light source 245 is wide so that it includes visible light as well as infrared light, such that it may use the infrared light for the inspection target which is out of range of the visible light, thereby improving the recognition. The light source 245 may emit white light having a wavelength of 400 to 800 nm.

The observation lens 242 may be disposed to face the inspection target to allow the line scan camera 243 or the auxiliary camera 244 to observe the inspection target via the observation lens 242. The size of the inspection target ranges from approximately tens of micrometers to several millimeters. Accordingly, the observation lens 242 is used to enlarge the inspection target. The resolution of the observation lens 242 may be, but is not limited to, approximately 1 μm.

The light emitted from the light source 245 is deflected by a first beam splitter 248 so that a part of the light is incident on the inspection target. For example, if the first beam splitter 248 is a half-mirror (or half transparent and half reflecting mirror), 50% of the incident light of 100% is reflected toward the inspection target while the other 50% of the incident light is transmitted. The amount of incident light back on the optical inspection unit 240 from the inspection target may vary depending on the inspection target. Approximately 30% of the light may be reflected by the inspection target to be incident back on the optical inspection unit 240. The amount of the light from the inspection target is decreased to 50% again while it passes through the first beam splitter 248. Subsequently, the light passes through a second beam splitter 249, i.e., a half-mirror, and the amount of the light is decreased to 50%, such that the 50% of the light is received by the auxiliary camera 243 while the other 50% of the light passes through the second beam splitter 249 and is received by the line scan camera 244. For example, assuming that the amount of the light emitted from the light source 245 is 100, the amount of light received by each of the line scan camera 243 and the auxiliary camera 244 is 3.75 (=100×50%×30%×50%×50%). That is, the amount of light that is reflected by the inspection target and actually received and analyzed is 3% to 4% of the amount of the initial light. Accordingly, it is effective to employ the light source 245 having a high power output. For example, the light source 245 may have a power output of 200 W or higher.

Actually, it may be difficult to recognize a transparent film by using the optical inspection unit 240 including the above-described elements only. Accordingly, the optical inspection unit 240 further includes a polarizer 246 and an analyzer 247 so as to effectively improve recognition of a transparent film and to measure the thickness.

The principles of determining whether there is an inspection target and measuring the thickness will be described with reference to FIG. 7. Incident light IL passing through the polarizer 246 is linearly polarized and is incident on the inspection target 24 to be inspected on the substrate 11. When the linearly polarized light is incident on the inspection target 24, a part of the light passes and the other part of the light is reflected. The light reflected by the inspection target 24 is referred to as reflect light 1 (RL1), and the light passing through the inspection target 24 is reflected by the surface of the substrate 11, which is referred to as reflect light 2 (RL2). Since the reflect light 2 (RL2) has passed through the inspection target 24 and then is reflected by the substrate 11, its wavelength, phase and amplitude are different from those of the reflect light 1 (RL1). In detail, the reflect light 1 (RL1) and the reflect light 2 (RL2) are circularly polarized and then pass through the analyzer 247. The lights having passed through the analyzer 247 are linearly polarized again. At this time, by analyzing the phase difference PD ($\Delta$) and the amplitude difference AD ($\Psi$) between the linearly polarized lights, it is possible to determine if there is the inspection target 24 and to measure the thickness. The phase difference and the amplitude difference may be referred to as a polarization difference.

Subsequently, descriptions will be made with reference to FIGS. 8A and 8B. FIG. 8A shows a wavelength graph of light having passed through an inspection target 24 thicker than that of FIG. 8B. As can be seen from FIG. 8A, the phase difference PD ($\Delta$) and the amplifier difference AD($\Psi$) between the reflect light 1 (RL1) and the reflect light 2 (RL2) are larger than in the graph of FIG. 8B. And, the amplitude of the mixed light ML in which the reflect light 1 (RL1) and the reflect light 2 (RL2) are combined is smaller than that of FIG. 8B. Therefore, the thicker the inspection target 24 is, the larger the phase difference PD ($\Delta$) and the amplitude difference AD ($\Psi$) are, and the smaller the amplitude of the mixed light ML is. The thickness of the inspection target 24 may be measured when the phase difference is 0 to $\lambda/2$, where $\lambda$ denotes wavelength.

The results of FIGS. 8A and 8B can be displayed as images, in which different amplitudes are displayed with different grey levels. The gray level represents the intensity of light, which is obtained by synthesizing the amplitude and phase of the wavelength of the light. For example, when the gray levels are set to 1 to 255, FIG. 8A may be displayed with the gray level 40, and FIG. 8B may be displayed with the gray level 200. The gray level 1 corresponds to black, while the gray level 255 corresponds to white. A lower gray level is displayed as a darker image.

The polarizer 246 is disposed between the light source 245 and the first beam splitter 248 to linearly polarize the light to be incident on the transparent film. The analyzer 247 is disposed between the transparent film and the line scan camera 243 so that the light that has passed through the transparent film and reflected is to be incident thereon. The light having passed through the analyzer 247 is an interfered light with different phases and amplitudes according to the transparent films having different thicknesses, and is received by the line scan camera 243. The line scan camera 243 synchronizes the amplitudes and phases of the received light by wavelength to send the synthesized information to the detection unit 250. The detection unit 250 analyzes the transparent film based on the transmitted information and determines whether the transparent film is defective.

In order to detect the thickness of the transparent film, samples of transparent films having different thicknesses are prepared in advance, and the intensities of light for the transparent films having different thicknesses are set, and the extracted data may be stored in the detection unit. The detection unit compares the intensity of light detected by the line scan camera 243 with the intensity of the lights prepared in advance, and extracts data. An image may be displayed based on the extracted data, and it is possible to determine whether there is a transparent film and to measure the thickness of the transparent film based on the displayed image.

Therefore, by further including the polarizer 246 and the analyzer 247, the optical inspection unit 240 generates the polarization difference between reflected lights to improve the recognition of the transparent film, thereby effectively determining whether there is a transparent film.

According to the above-described inspection manner, the time for detecting a defect of an inspection target may be equal to the time for scanning the inspection target. This is because the processes of comparing the intensities of the lights and detecting a defect by the detection unit 250 are carried out during the process of scanning the inspection target. In detail, the optical inspection unit 240 scans along the inspection area of the inspection target once in the x-axis or the y-axis direction. Subsequently, during the scanning along the next inspection area, a process of comparing the data of the previously scanned inspection area with the data stored in the detection unit and analyzing datum are performed, to determine whether there is a defect. By doing so, the inspection time of the inspection target can be reduced.

The aspects of the present disclosure can also be described as follows:

According to an aspect of the present disclosure, there is provided an inspection method comprises irradiating an inspection target with light using a polarizer, receiving reflective light that is reflected by the inspection target and passes through an analyzer by a line scan camera, synthesizing an amplitude and a phase of wavelength of the reflective light into an intensity of light, comparing the intensity of the light with predetermined intensities of light for inspection targets having different thicknesses, and detecting a defect of the inspection target based on the compared intensity with the predetermined intensities. It can be determined whether there is a transparent film, and the thickness of the transparent film can be measured in a large area. The inspection is carried out in real-time after the transparent film is formed, such that if a defect is generated, it can be fed back immediately to thereby reduce defects. In this case, the processing cost can be saved.

The comparing the intensity of the light with predetermined intensities of light may be carried out while a new inspection area of the inspection target is scanned.

The inspection target may be a transparent film on an organic light emitting panel, and the comparing the intensity of the light with predetermined intensities of light may include detecting existence of the transparent film and measuring a thickness of the transparent film.

The detecting existence of the transparent film may comprise detecting whether the transparent film is formed in at least one of a bending area of the organic light emitting panel, a pad of the organic light emitting panel or a scribing line on a substrate of the organic light emitting panel.

The detecting existence of the transparent film may include comparing an intensity of a metal key covered by the transparent film with an intensity of a metal key not covered by the transparent film among a plurality of metal keys disposed on the inspection target.

The measuring the thickness of the transparent film may include measuring the thickness of the transparent film deposited on a test pattern disposed on the organic light emitting panel.

According to another aspect of the present disclosure, there is provided an inspection apparatus comprises a polarizer linearly polarizing light emitted from a light source, an analyzer allowing the light reflected by an inspection target that passes through the polarizer to transmit, an optical inspection unit including a line scan camera that receives the light transmitted the analyzer and synthesizes an amplitude and a phase of wavelength of the reflected light into an intensity of light, and a detection unit comparing the intensity of the light with predetermined intensities of light for inspection targets having different thicknesses, and detecting a defect of the inspection target based on results of the comparing. The recognition of the transparent film can be improved, and the entire area of the substrate can be inspected. In this case, it is possible to effectively determine whether there is a transparent film and to measure the thickness.

The inspection apparatus may further comprise a beam splitter that separates the linearly polarized light so that it is incident on the inspection target.

The inspection apparatus may further comprise a second beam splitter including a half-mirror reducing an amount of the light transmitted through the analyzer to 50%.

The first beam splitter may include a half-mirror.

The light emitted from the light source may have a wavelength of 400 to 800 nm.

The inspection apparatus may further comprise an alignment camera configured to align the inspection target with the optical inspection unit.

The apparatus may further comprise an auto focusing unit automatically adjusting focus of the optical inspection unit with respect to the inspection target when the optical inspection unit moves along an inspection area of the inspection target.

The optical inspection unit may further comprise an auxiliary camera configured to align a scan area in order to scan the inspection area of the inspection target.

The auxiliary camera may receive 50% of the light passed through the second beam splitter while the line scan camera receives the other 50% of the light passes through the second beam splitter.

The inspection target may include a transparent film disposed in a cell for an organic light emitting panel.

The transparent film may include of a silicon or acrylic material.

The line scan camera may observe an area of 8 mm by 8 mm at a time while moving.

The line scan camera may inspect existence of the inspection target and measuring a thickness of the inspection target.

The optical inspection unit may further comprise a lens barrel accommodating a plurality of lenses adjusting an optical path and the light source.

Thus far, aspects of the present disclosure have been described in detail with reference to the accompanying drawings. However, the present disclosure is not limited to the aspects, and modifications and variations can be made thereto without departing from the technical idea of the present disclosure. Accordingly, the aspects described herein are merely illustrative and are not intended to limit the scope of the present disclosure. The technical idea of the present disclosure is not limited by the aspects. Therefore, it should be understood that the above-described aspects are not limiting but illustrative in all aspects. The scope of protection sought by the present disclosure is defined by the appended claims and all equivalents thereof are construed to be within the true scope of the present disclosure.

What is claimed is:

1. An inspection method comprising:
providing an inspection target on a substrate having a plurality of metal keys disposed between a plurality of cells;
using a polarizer to linearly polarize incident light emitted from a light source;
using a first beam splitter to direct a portion of the linearly polarized incident light onto the inspection target;
using an analyzer to linearly polarize circularly polarized reflective light, which is reflected from the inspection target and passes back through the first beam splitter;
using a line scan camera to receive the linearly polarized reflective light, linearly scan test patterns located along an X-axis direction on the inspection target and linearly scan test patterns located along a Y-axis direction on the inspection target, which passes through the analyzer and a second beam splitter, to obtain an intensity of light based upon amplitude and phase characteristics in accordance with wavelengths of the linearly polarized reflective light received by the line scan camera, and to compare the intensity of the light with predetermined intensities of light of the inspection targets having different thicknesses; and
using a detector to detect potential defects of the inspection target based on results of the comparing of the intensity of light with the predetermined intensities of light,
wherein the using the line scan camera comprises detecting existence of the inspection target and measuring a thickness of the inspection target while the line scan camera moves along the plurality of metal keys.

2. The method of claim 1, wherein the comparing the intensity of the light with predetermined intensities of light is carried out while a new inspection area of the inspection target is scanned.

3. The method of claim 1, wherein the inspection target is a transparent film on an organic light emitting panel.

4. The method of claim 1, wherein the detecting existence of the inspection target comprises detecting whether the inspection target is formed in at least one of a bending area of an organic light emitting panel, a pad of the organic light emitting panel or a scribing line on the substrate of the organic light emitting panel.

5. The method of claim 4, wherein the detecting existence of the inspection target comprises comparing an intensity of light reflected off the test patterns including a metal key covered by the inspection target with an intensity of light reflected off a metal key not covered by the inspection target among the plurality of metal keys disposed on the inspection target.

6. The method of claim 1, wherein the measuring the thickness of the inspection target comprises measuring the thickness of the inspection target deposited on the test patterns disposed on the organic light emitting panel.

7. An inspection apparatus comprising:
a polarizer to linearly polarize incident light emitted from a light source;
a first beam splitter to direct a portion of the linearly polarized incident light passed through the polarizer onto a plurality of metal keys on an inspection target;
an analyzer to linearly polarize circularly polarized reflective light, which is reflected from the inspection target and passes back through the first beam splitter;
a line scan camera to receive the linearly polarized reflective light, linearly scan test patterns located along an X-axis direction on an inspection target and linearly scan the test patterns along a Y-axis direction on the inspection target, which passes through the analyzer and a second beam splitter, to obtain an intensity of light based upon amplitude and phase characteristics in accordance with wavelengths of the linearly polarized reflective light received by the line scan camera, and to compare the intensity of the light with predetermined intensities of light of inspection targets having different thicknesses; and
a detector to detect potential defects of the inspection target based on results of the comparing of the intensity of light with the predetermined intensities of light,
wherein the line scan camera detects existence of the inspection target and measures a thickness of the inspection target while the line scan camera moves along the metal keys.

8. The apparatus of claim 7, wherein the first beam splitter separates the linearly polarized incident light so that it is incident on the inspection target.

9. The apparatus of claim 8, the second beam splitter including a half-mirror reducing an amount of the light transmitted through the analyzer to 50%.

10. The apparatus of claim 9, wherein the optical inspection unit further comprises an auxiliary camera configured to align a scan area in order to scan the inspection area of the inspection target.

11. The apparatus of claim 10, wherein the auxiliary camera receives 50% of the linearly polarized reflective light passed through the second beam splitter while the line scan camera receives the other 50% of the linearly polarized reflective light passes through the second beam splitter.

12. The apparatus of claim 9, wherein the optical inspection unit further comprises a lens barrel accommodating a plurality of lenses adjusting an optical path and the light source.

13. The apparatus of claim 8, wherein the first beam splitter includes a half-mirror.

14. The apparatus of claim 7, wherein the incident light emitted from the light source has a wavelength of 400 to 800 nm.

15. The apparatus of claim 7, further comprising an alignment camera configured to align the inspection target with the line scan camera.

16. The apparatus of claim 7, further comprising an auto focusing unit automatically adjusting focus of the optical inspection unit with respect to the inspection target when the line scan camera moves along an inspection area of the inspection target.

17. The apparatus of claim 7, wherein the inspection target includes a transparent film disposed in a cell for an organic light emitting panel.

18. The apparatus of claim 17, wherein the transparent film includes a silicon or acrylic material.

19. The apparatus of claim 7, wherein the line scan camera observes an area of 8 mm by 8 mm at a time while moving.

* * * * *